(12) United States Patent
Diefenbach

(10) Patent No.: US 12,090,306 B2
(45) Date of Patent: Sep. 17, 2024

(54) WIRELESS ELECTRONICS ASSEMBLY FOR INJECTION DEVICES

(71) Applicant: SANOFI, Paris (FR)

(72) Inventor: Holger Diefenbach, Frankfurt am Main (DE)

(73) Assignee: Sanofi, Paris (FR)

( * ) Notice: Subject to any disclaimer, the term of this patent is extended or adjusted under 35 U.S.C. 154(b) by 1163 days.

(21) Appl. No.: 16/763,743

(22) PCT Filed: Nov. 12, 2018

(86) PCT No.: PCT/EP2018/080883
§ 371 (c)(1),
(2) Date: May 13, 2020

(87) PCT Pub. No.: WO2019/096719
PCT Pub. Date: May 23, 2019

(65) Prior Publication Data
US 2021/0369972 A1 Dec. 2, 2021

(30) Foreign Application Priority Data

Nov. 14, 2017 (EP) ..................................... 17306575

(51) Int. Cl.
*A61M 5/315* (2006.01)
*A61M 5/24* (2006.01)

(52) U.S. Cl.
CPC .......... *A61M 5/31568* (2013.01); *A61M 5/24* (2013.01); *A61M 2205/3327* (2013.01);
(Continued)

(58) Field of Classification Search
CPC ................ A61M 5/31568; A61M 5/24; A61M 2205/3389; A61M 2205/06063;
(Continued)

(56) References Cited

U.S. PATENT DOCUMENTS 4,973,318 A * 11/1990 Holm ..................... A61M 5/24
604/218
2017/0189621 A1* 7/2017 Rodiera Olivé .. A61M 39/0247
2017/0316177 A1* 11/2017 Mirov ................... A61M 5/315

FOREIGN PATENT DOCUMENTS

JP 2012-507314 3/2012
JP 2017-531454 10/2017
(Continued)

OTHER PUBLICATIONS

PCT International Preliminary Report on Patentability in Application No. PCT/EP2018/080883, dated May 19, 2020, 8 pages.
(Continued)

*Primary Examiner* — Lauren P Farrar
(74) *Attorney, Agent, or Firm* — Fish & Richardson P.C.

(57) ABSTRACT

Electronics assemblies with wireless capabilities for use in a drug delivery device. At least one of the electronics assemblies includes a processor, a sensor arranged to measure a fill level of a drug container and output a measurement to the processor, a wireless module to which an external device can be paired, a power module arranged to supply power to the assembly, and memory storing instructions for the processor to perform. The instructions include activating the sensor at a first time interval and receiving the measurement signal, for each activating of the sensor at the first time internal, determining, based on the received measurement signal, a change in the fill level of the drug container, and when the change in the fill level is detected, activating the wireless module for a first duration to enable the external device to pair with the wireless module.

20 Claims, 8 Drawing Sheets

(52) U.S. Cl.
CPC ............... *A61M 2205/3375* (2013.01); *A61M 2205/3389* (2013.01); *A61M 2205/3553* (2013.01); *A61M 2205/50* (2013.01); *A61M 2205/8206* (2013.01)

(58) Field of Classification Search
CPC .... A61M 2205/6072; A61M 2205/609; A61M 2205/3327; A61M 2205/3375; A61M 2205/3553; A61M 2205/50; A61M 2205/8206
See application file for complete search history.

(56) References Cited

FOREIGN PATENT DOCUMENTS

| WO | WO 2010/052275 | 5/2010 | |
|----|----------------|--------|---|
| WO | WO 2014/106096 | 7/2014 | |
| WO | WO 2016/019375 | 2/2016 | |
| WO | WO-2016019375 A1 * | 2/2016 | ......... A61B 5/14532 |
| WO | WO 2016/134137 | 8/2016 | |
| WO | WO 2016/166338 | 10/2016 | |
| WO | WO 2017/189153 | 11/2017 | |

OTHER PUBLICATIONS

PCT International Search Report and Written Opinion in Application No. PCT/EP2018/080883, dated Jan. 16, 2019, 11 pages.

* cited by examiner

WIRELESS ELECTRONICS ASSEMBLY FOR INJECTION DEVICES

CROSS REFERENCE TO RELATED APPLICATIONS

The present application is the national stage entry of International Patent Application No. PCT/EP2018/080883, filed on Nov. 12, 2018, and claims priority to Application No. EP 17306575.6, filed on Nov. 14, 2017, the disclosures of which are incorporated herein by reference.

TECHNICAL FIELD

This description relates to an electronics assembly with wireless capabilities for use in a drug delivery device.

BACKGROUND

A variety of diseases exist that require treatment by injection of a medicament. Such injections can be performed using drug delivery devices, which can be applied either by medical personnel or by patients themselves. As an example, type-1 and type-2 diabetes can be treated by patients themselves by injection of drug doses, for example once or several times per day. For instance, a pre-filled disposable drug pen or autoinjector can be used as a drug delivery device. Alternatively, a re-usable pen or autoinjector may be used. A re-usable pen or autoinjector allows replacement of an empty medicament cartridge by a new one. Either type of pen or autoinjector may come with a set of one-way needles that are replaced before each use.

SUMMARY

This disclosure relates to drug delivery devices having electronics capable of detecting certain properties related to the drug delivery device, such as the fill level of medicament within a cartridge in the drug delivery device, and wirelessly transmitting those detected properties to an external device, such as a mobile phone, tablet, or computer, for a user to view. In certain cases, the electronics are housed within a bung or stopper of the cartridge.

In a representative overview, an electronics assembly is inserted into the bung of the cartridge. The electronics assembly detects the fill level of the cartridge (e.g., by detecting a position of the bung), and, in some instances, the temperature of the cartridge or medicament therein. The fill level in the cartridge varies as the patient uses the device and the electronics assembly senses this change at a short time interval (e.g., 5 minutes) and this level change activates a Bluetooth transmitter at the moment the detection is sensed. Thereafter, the patient is able to pair or link an external device with the electronics assembly to activate a transmission of the measured data (e.g., the delivered dose). After a short time (e.g., 10 minutes), if no further change in the fill level in the cartridge has been measured and no external device has been paired, the Bluetooth transmitter can again be automatically set to sleep mode and the electronics assembly resumes sensing at regular intervals for the next drug delivery operation. After each detected injection, a new transfer of the device with the external device is possible. As an additional feature, a printed variable data (i.e., a batch or expiration date) or the material code of the label can be used when paired. These can either be read with a camera or can be entered manually by the patient in order to confirm that the data received from the electronics assembly matches the drug delivery device.

In a representative example, an electronics assembly is arranged in a cartridge or otherwise positioned in a drug delivery device to enable a sensor of the electronics assembly to detect changes in the cartridge or a drive mechanism of the drug delivery device that is used for changing the fill level of the cartridge (e.g., a filling operation and a drug delivery operation). The electronics assembly includes a processor configured to initiate data exchange via Bluetooth wireless module, or similar wireless protocol, upon determining a change in fill level. In a first state, the processor instructs the sensor to obtain measurements at a very low frequency, e.g., once every several days, and the wireless module is deactivated. This state is active before assembly or before filling of the cartridge. After the bung including electronics is assembled with the cartridge, a response can be measured, such as an indication that a medicament has been introduced to the cartridge or that the cartridge has been assembled into the drug delivery device. This detection of the trusted response triggers the processor to switch the activation of the sensor to a higher frequency of measurements, e.g., once every several minutes. In some instances, the wireless module is activated at this time, which enables pairing with an external device to send out current measurement for a short period. Alternatively, the wireless module can be activated each time a change in measurement results is determined by the processor to further reduce power consumption as the wireless module is only activated for "new" measured values and not for every measurement. A benefit of this arrangement is that no external activation of the electronics assembly is required, which enables the electronics assembly to be a self-contained (e.g., sealed) assembly after production and before introduction to the cartridge or drug delivery device.

Examples of the electronics assembly can be used in both single-use (e.g., disposable) drug delivery devices, and multi-use (e.g., reusable) drug delivery devices. In an example disposable embodiment, the electronics assembly is constructed and inserted into a cartridge, at which point the electronics assembly is sensing the cartridge in the low-frequency sensing mode waiting to detect the introduction of the medicament, which indicates the completion of the assembly of the disposable drug delivery device. With the detection of the medicament, the disposable drug delivery device is ready to be used, and thus the electronics assembly enters into the high-frequency sensing mode and awaits detection of a drug-delivery operation, at which time the electronics assembly activates the wireless module to allow pairing with an external device for a short time period. In an alternative embodiment, the electronics assembly lacks an initial low-frequency sensing mode and instead includes an activation mechanism or sensor configured to detect assembly of the disposable drug delivery device and activate the high-frequency sensing mode. This activation mechanism may be a switch arranged on the electronics assembly to be trigger by contact with the drug delivery device during assembly.

In a reusable drug delivery device example, an electronics assembly is constructed and assembled with a pre-filled cartridge, at which point the electronics assembly may be in a low-frequency sensing state with a sensor configured to detect, for example, the assembly of the pre-filed cartridge into the drug delivery device, or the electronic assembly may be in the high-frequency sensing mode upon instruction of the medicament to the cartridge and prior to the cartridge's instruction to the drug delivery device. In either of the above single-use and multi-use drug delivery device examples, the electronics assembly uses a sensor or activation mechanism to enter a high-frequency sensing mode when the drug delivery devices are ready to be used, thereby enabling faster detection of a subsequence drug delivery operation and faster activation of the wireless module for a given duration after the detection of the drug delivery operation.

Certain aspects of the present disclosure result in several advantages beyond the addition of wireless connectivity to the drug delivery device. For example, a sealed electronics assembly with an internal power source has a limited shelf life due to the finite amount of internal power By limiting sensor activation prior to the drug delivery device entering a ready-to-use configuration, the shelf life of a manufactured electronics assembly prior to introduction to a drug delivery device or cartridge can be extended. Similarly, by limiting wireless module activation after a drug delivery operation, the shelf life of the electronics assembly after final manufacturing of the drug delivery device (i.e., in a ready to use state) can be extended. With an extended shelf life, electronics assemblies can be manufactured separately and independently from the manufacturing of the cartridge or drug delivery device, which also reduces or eliminates impact on existing production lines.

Another advantage is the ability for the electronics assembly to provide extra information to a user via the wireless transmission to the external device. For example, the drug delivery device or cartridge may be provided with an expiration date that can be transmitted to and stored in the external device to help the user confirm the printed information and better manage the drug delivery. Additional information, such as a batch number or unique serial number of the drug delivery device or cartridge can be transmitted to the external device to aid the user. This data can also be centrally tracked by the manufacturer to assist in recalls, track and analyze patient behavior, and monitor product usage. Additionally, in some embodiments, the electronics assembly includes a temperature sensor and the electronics assembly can provide temperature data to the external device to, for example, warn a user when a temperature limit has been reached. This also allows a manufacturer to track patient and transporter compliance with medicament temperature handling policies.

An example embodiment of the present disclosure is an electronics assembly for use in a drug delivery device. The electronics assembly includes a processor, a sensor arranged to measure a fill level of a drug container of the drug delivery device and output a measurement signal to the processor; a wireless module to which an external device can be paired, a power module arranged to supply power to the sensor, the processor, and the wireless transmitter, and at least one non transitory computer readable medium storing instructions operable to cause the processor to perform operations. The operations include activating the sensor at a first time interval and receiving the measurement signal, for each activating of the sensor at the first time internal, determining, based on the received measurement signal, a change in the fill level of the drug container, and when the change in the fill level is detected, activating the wireless module for a first duration to enable the external device to pair with the wireless module.

In some instances, the instructions stored include, when the wireless module is paired, transmitting the change in the fill level of the drug container to the external device and deactivating the wireless module.

In some instances, the electronics assembly includes a switch arranged to be activated by assembly of the electronics assembly into the drug delivery device such that the switch activates the electronics assembly.

In some instances, the instructions include prior to activating the sensor at the first time interval, activating the sensor at a second time interval and receiving the measurement signal, the second time internal being longer than the first time internal, determining, based on the received measurement signal, if the drug container is empty or filled, and when the drug container is determined to be filled, stopping the activating of the sensor at the second time internal, and commencing the activating of the sensor at the first time internal.

In some instances, the first time internal is less than one hour. In some instances, the second time internal is more than 12 hours. In some instances, the first duration is less than 30 minutes.

In some instances, the instructions include determining a remaining power level of the power module, and adjusting the first duration based on the remaining power level. In some instances, the instructions include storing each change in the fill level of the drug container in the memory, and when the wireless module is paired, transmitting each of the stored changes in the fill level of the drug container to the external device and deactivating the wireless module.

In some instances, the sensor is arranged to be disposed inside of a bung, and wherein the bung is configured to be inserted into the drug container. In some instances, the electronics assembly is configured to be inserted into the bung. In some instances, the electronics assembly and/or the sensor is integrally formed with the bung.

In some instances, the sensor is configured to measure the fill level of the drug container by measuring a position of the bung in the drug container. In some instances, the instructions include calculating the fill level of the drug container based on the sensed position of the bung. In some instances, sensor includes an ultrasonic transmitter and corresponding detector, the ultrasonic transmitter configured to emit an ultrasonic signal into the drug container, and the corresponding detector being configured to receive a reflection of the ultrasonic signal from the drug container and output the measurement signal to the processor. In some instances, the external electronics device is selected from the following: a smart phone, a smart watch, a tablet, and a personal computer.

In some instances, the drug delivery device or the drug container comprises printed identification or expiration information, and wherein the instructions include, when the wireless module is paired, transmitting confirmation identification corresponding to the printed identification or expiration information.

Another example of the present disclosure is a method of activating a wireless module of an electronics assembly configured to be inserted into a drug container of a drug delivery device. The method includes activating a sensor of the electronics assembly at a first time interval and receiving a measurement signal from the sensor, the sensor being arranged to measure a fill level of the drug container, for each activating of the sensor at the first time internal, determining, based on the received measurement signal, a change in the fill level of the drug container, and when the change in the fill level is detected, activating a wireless module of the electronics assembly for a first duration and enabling an external device to pair with the wireless module.

In some instances, the method includes when the wireless module is paired, transmitting the change in the fill level of the drug container to the external device and deactivating the wireless module In some instances, the method includes prior to activating the sensor at the first time interval, activating the sensor at a second time interval and receiving the measurement signal, the second time internal being longer than the first time internal, determining, based on the received measurement signal, if the drug container is empty or filled, and when the drug container is determined to be filled, stopping the activating of the sensor at the second time internal, and commencing the activating of the sensor at the first time internal.

In some instances, the first time interval is less than an hour. In some instances, the second time interval is more than 12 hours.

In some instances, the method includes storing each change in the fill level of the drug container in the memory, and when the wireless module is paired, transmitting each of the stored changes in the fill level of the drug container to the external device and deactivating the wireless module.

In some instances, the method includes determining a remaining power level of a power module of the electronics assembly, and adjusting the first duration based on the remaining power level.

Yet another example of the present disclosure is a system including a drug delivery device comprising a housing, a drug container configured to be contained in the housing of the drug delivery device, and a bung disposed in a cavity of the drug container and configured to be driven into the drug container by a drive mechanism of the drug delivery device. The bung or the drug container comprises an electronics assembly includes a processor, a sensor arranged to measure a fill level of the drug container and output a measurement signal to the processor, a wireless module to which an external device can be paired, a power module arranged to supply power to the sensor, the processor, and the wireless transmitter, and a non-transitory computer readable medium storing instructions operable to cause the processor to perform operations. The instructions include activating the sensor at a first time interval and receiving the measurement signal, for each activating of the sensor at the first time internal, determining, based on the received measurement signal, a change in the fill level of the drug container, and when the change in the fill level is detected, activating the wireless module for a first duration to enable the external device to pair with the wireless module.

DETAILED DESCRIPTION

Figure 1:
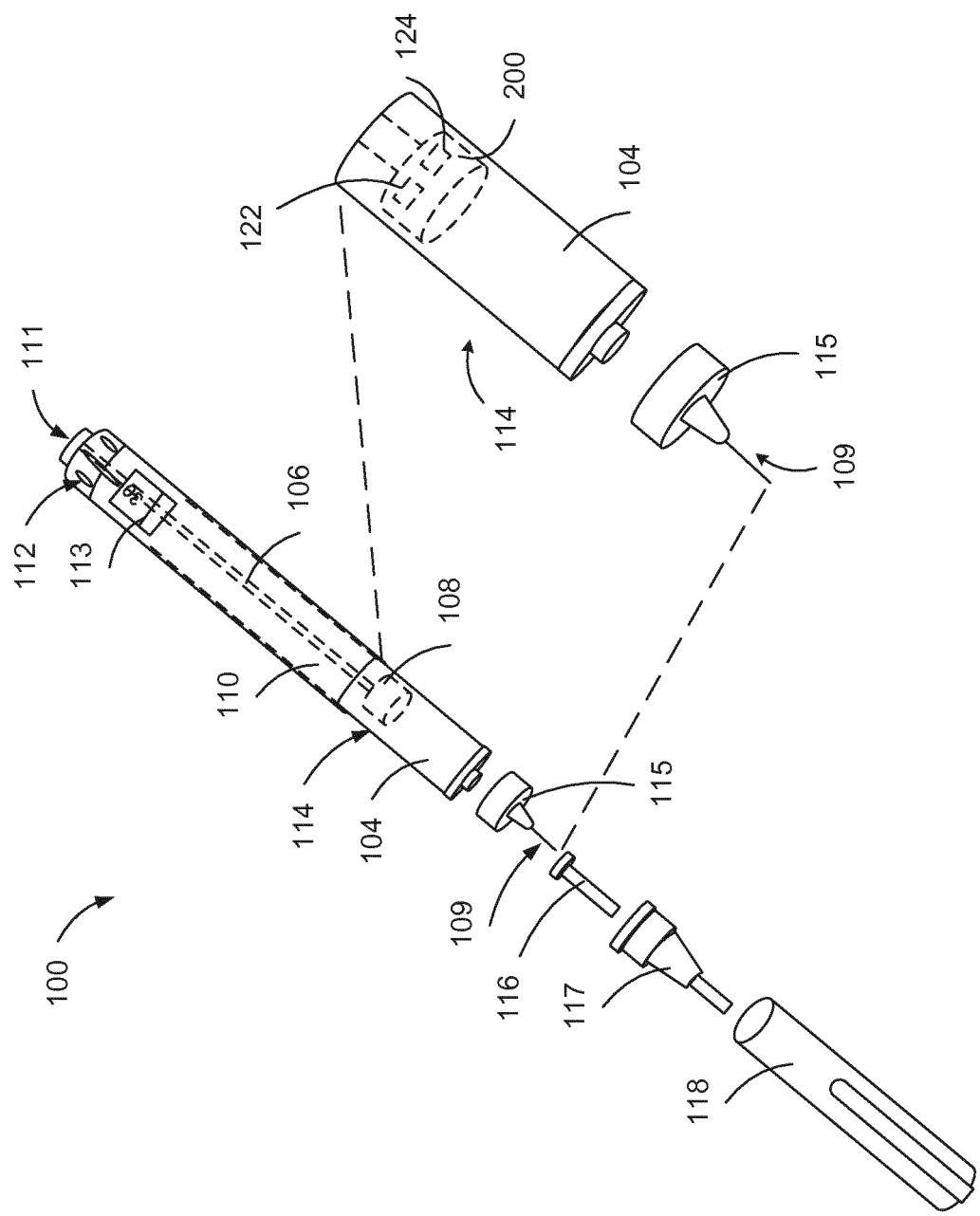
FIG. 1 is an exploded view of a drug delivery device.

Some cartridge-based injection and medical syringe systems include integrated electronics that support wireless connectivity. In some examples, a cartridge stopper (sometimes referred to as a bung) can include a self-contained electronics assembly, including a sensor, a wireless module, a power module, and a processor with memory. For example, a stopper may accept an insertable electronic assembly that is separated from the stopper. The stopper, for example, can be assembled into the stopper or cartridge after sterilization. The electronics assembly can be a self-contained unit that is constructed prior to assembly of the drug delivery device and embedded in the stopper during a final assembly of the drug delivery device. In some examples, the self-contained electronics assembly enables detection of the fill level of the cartridge and enables pairing (e.g., via Bluetooth or similar wireless protocols) with an external device to report the measured fill level. For example, a drug delivery device with a wireless module may enable a smartphone or tablet to pair with the drug delivery device to confirm that an injection has taken place or to receive a measurement from an internal sensor providing a confirmation or measurement of an expelled dose.

Regardless of the information provided, there exists a challenge in balancing the power requirements of an internal wireless module with the size and shelf life limitations of typical on-board sources of power. Two particular examples of challenges, discussed in more detail below, involve (1) how to extend the shelf life of an integrated electronics assembly prior to assembly of the drug delivery device or filling of a cartridge has occurred, and (2) how to further extend the operational life of the integrated electronics assembly post assembly or filling when use of the wireless module is necessary. In some examples of the present disclosure, a solution to the first challenge involves using a sensor to detect when the medicament is filled in the cartridge and subsequently changing to a response detection mode to be responsive to subsequent injections, as described in more detail below. In addition, in some examples, a solution to the second challenge involves limiting the operation, and thus the power drain, of a wireless module to short intervals after detection of an injection, as described in more detail below.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within defined parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package, cartridge, or "drug container" adapted for use with a drug delivery device. The drug container may be, for example, a cartridge, syringe, reservoir, or other vessel configured to provide a suitable chamber for storage (e.g., short- or long-term storage) of one or more pharmaceutically active compounds. For example, in some embodiments, the chamber may be designed to store a drug for at least one day (e.g., 1 to at least 30 days). In some embodiments, the chamber may be designed to store a drug for about 1 month to about 2 years. Storage may occur at room temperature (e.g., about 20° C.), or refrigerated temperatures (e.g., from about −4° C. to about 4° C.). In some embodiments, the drug container may be or may include a dual-chamber cartridge configured to store two or more components of a drug formulation (e.g., a drug and a diluent, or two different types of drugs) separately, one in each chamber. In such embodiments, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance that is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta-'decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-114, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure can include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

FIG. 1 is an exploded view of a drug delivery device 100, which may be a disposable or reusable drug delivery device. The drug delivery device 100 includes a housing 110 that contains a cartridge 114 and a cartridge housing 104 in which the cartridge 114 is disposed. A bung or stopper 200 is disposed in the body 104 of the cartridge 114 and can be advanced within the body 104 during use to expel medicament from the cartridge 113. A needle assembly 115 can be affixed to the cartridge housing 104. A needle 109 of the needle assembly 115, prior to use, is protected by an inner needle cap 116 and an outer needle cap 117, which in turn can be covered by a cap 118. A medicament or drug dose to be ejected from the drug delivery device 100 is selected by turning a dosage knob 112, and the selected dose is displayed via a dosage window or display 113.

As described further below, the drug delivery device 100 may include one or more electronic components 122, 124, some of which may be included in the stopper 200 of the cartridge 114, for example, as a self-contained electronics assembly. In some examples, the electronic components 122, 124 are located in other parts of the drug delivery device, while enabling a sensor of the electronic components 122, 124 to determine or measure the fill level of the cartridge 114.

Continuing with the operation of the drug delivery device 100, turning the dosage knob 112 causes a mechanical click sound to provide acoustical feedback to a user. The numbers displayed in the dosage display 113 are printed on a sleeve that is contained in the housing 110 and mechanically interacts with a plunger configured to interact with the cartridge 114. When the needle 109 is stuck into a patient and then an injection button 111 is pushed, the drug dose displayed in the display 113 will be ejected from the drug delivery device 100. During an injection, a drive mechanism 106, which is shown as an outline of a plunger arm, drives the stopper 200 into the cartridge 114 to expel the drug. The stopper 200 acts as a barrier to prevent fluids and gases from leaking in and out of the cartridge 114, and can prevent evaporation of H2O and other fluids. In some embodiments, the seal function is provided by elastic sealing elements in contact with the container walls, but still allows the stopper 200 to glide. When the needle 109 of the drug delivery device 100 remains for a certain time in the skin of the patient after the injection button 111 is pushed, a high percentage of the dose is actually injected into the patient's body. In some examples, the drug delivery device 100 is a single use or disposable device, and one skilled in the art will appreciate that the electronic components 122, 124 used in the drug delivery device 100 can be similarly present with similar functions in a single use or disposable drug delivery device.

Figure 2B:
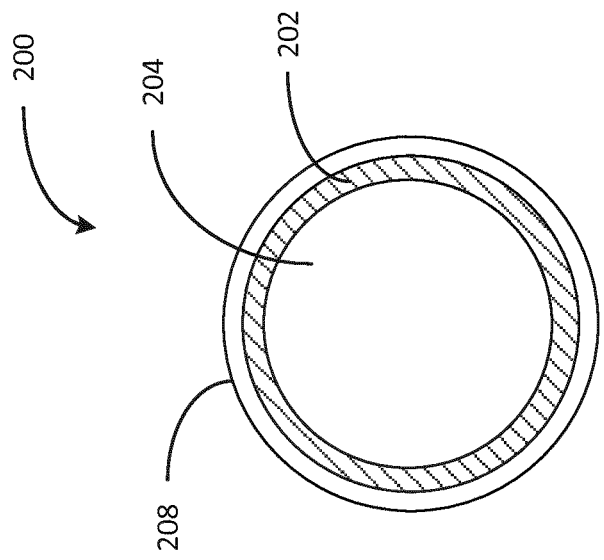
FIG. 2B is a top view of the stopper of FIG. 2A.
Figure 2A:
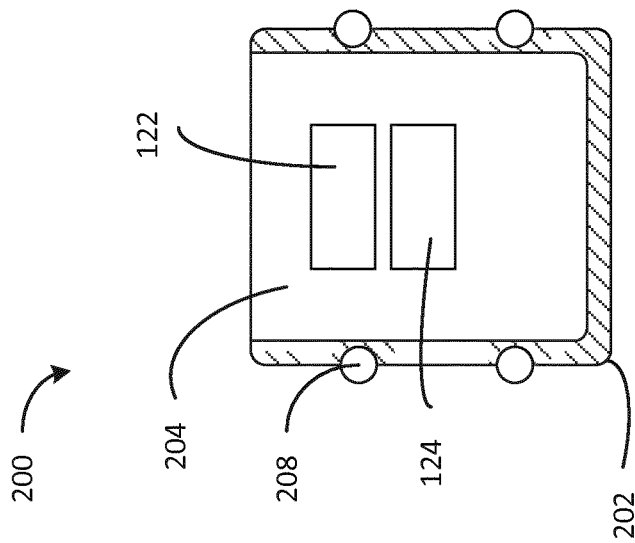
FIG. 2A is a cross sectional view of the stopper of FIG. 1 containing an electronics assembly.

FIG. 2A is a cross sectional view of an embodiment of the stopper 200 of the drug delivery device 100. The stopper 200 includes a shell 202 and a core 204 containing the electronic devices 122, 124, which, in some embodiments, are embedded into the material of the core 204. In some instances, the core 204 is configured to be inserted into the shell 202 of the stopper 200 after manufacturing. For example, the core 204 may be inserted into the shell 202 after the shell is disposed in the cartridge 114 of the drug delivery device 100. In other instances, the shell 202 is assembled with the core 204 having the electronic devices 122, 124 to be later inserted into the cartridge 114. In some instances, the shell 202 includes sealing elements 208 (e.g. o-rings) that are arranged to provide a sealing interface with an inner surface of the cartridge 114 when the shell 202 is inserted into the cartridge 114. In some instances, the shell 202 and core 204 are manufactured as a single component with or without the electronic devices 122, 124.

In some instances, the materials of the shell 202 and the core 204 are selected for their ability to allow a sensor signal to pass therethrough. For example, nonmetal materials like polymers or ceramics or very thin metal (e.g., <0.1 mm in thickness) may be used. The electronic devices 122, 124 may include, for example, a sensor, an energy source, a microcontroller, and/or a wireless transceiver. The electronic devices 122, 124 are representative only. There can be any number of electronic devices. The sensor may be a sensor/transceiver device such as, for example, a piezoelectric device, an acoustic sensor, or an electromagnetic sensor. The sensor/transceiver may transmit a signal, such as, for example, an ultrasonic, acoustic, light, or other signal through the stopper 200 and measure a response which may, in some embodiments, be used to determine the position of the stopper 200 in the cartridge 114 or if an injection has occurred. In some embodiments, the sensor comprises an ultrasonic sensor, having an ultrasonic emitter and an acoustic sensor, where the sensor is arranged to emit an ultrasonic signal into the cartridge 114 using the ultrasonic emitter, and the acoustic sensor is positioned to receive a reflection of the ultrasonic signal from the cartridge 114 that is effected by the fill level of a medicament in the cartridge 114 or the presence of a medicament in the cartridge 114. The position of the stopper 200 before and after an injection corresponds to a change in volume of medicament remaining in the cartridge 114, which can indicate the volume or dose of the medicament expelled from the cartridge 114. In some embodiments, the response received by the sensor is provided to a controller (e.g. a processor located in the stopper 200 or elsewhere in the drug delivery device 100) which may receive the response and calculate a state of the cartridge 114. The state of the cartridge 114 may correspond to a fill level of medicament in the cartridge 114, a position of the stopper 200, or the volume of a dose.

In some embodiments, the energy source is a battery or an energy storing device. The wireless module may communicate with an external electronic device as well as with the sensor and energy source. The external electronic device, which may be a controller, smart phone, tablet, or computer, may communicate data received from the sensor to an external database. The communication with the external device can be one way or bidirectional. Data transferred from the sensor device to an external database can contain information which is related to the identity of the device (e.g. a unique number), calibration data, production lot information, device material information, data related to storage time and production time, and information related to the sensor measurement (e.g., time of measurement, sensor measurement results like temperature, distances, light signals, and acoustic signals, etc.). The wireless module may communicate using any known wireless communication technique including, for example Bluetooth, NFC, or radio frequencies.

The shell 202 of the stopper 200, in some embodiments, is constructed from materials such as metals, polymers (e.g., COC, PA, PP, PE, POM, PS, ABS, COP, etc.), glass or ceramics. In some embodiments, the electronic devices (or electronic assembly) 122, 124 includes one or more of the following: a sensor, a power source (e.g. battery), a controller or processor, a wireless communication module (e.g. Bluetooth, NFC, Bluetooth LE, any RF, IrDA), memory, an on-off switch, a thermos-sensing element, a pressure sensor etc. In some embodiments, the electronics devices 122, 124 include an on-off mechanism configured to trigger the electronics devices 122, 124 by, for example, contact on the stopper 200 by a component of the drug delivery device 100 (e.g., force from a drive mechanism 106) during assembly of the drug delivery device 100.

FIG. 2B is a top view of the stopper 200. The shell 202 surrounds the core 204 and interfaces with the sealing element 208, which forms a sealing interface with the cartridge 114 upon the stopper's 200 introduction into the cartridge 114. The sealing interface may form at least part of a sterile barrier within the cartridge 114 to preserve the sterility of the medicament to be delivered by the drug delivery device 100.

Figure 2C:
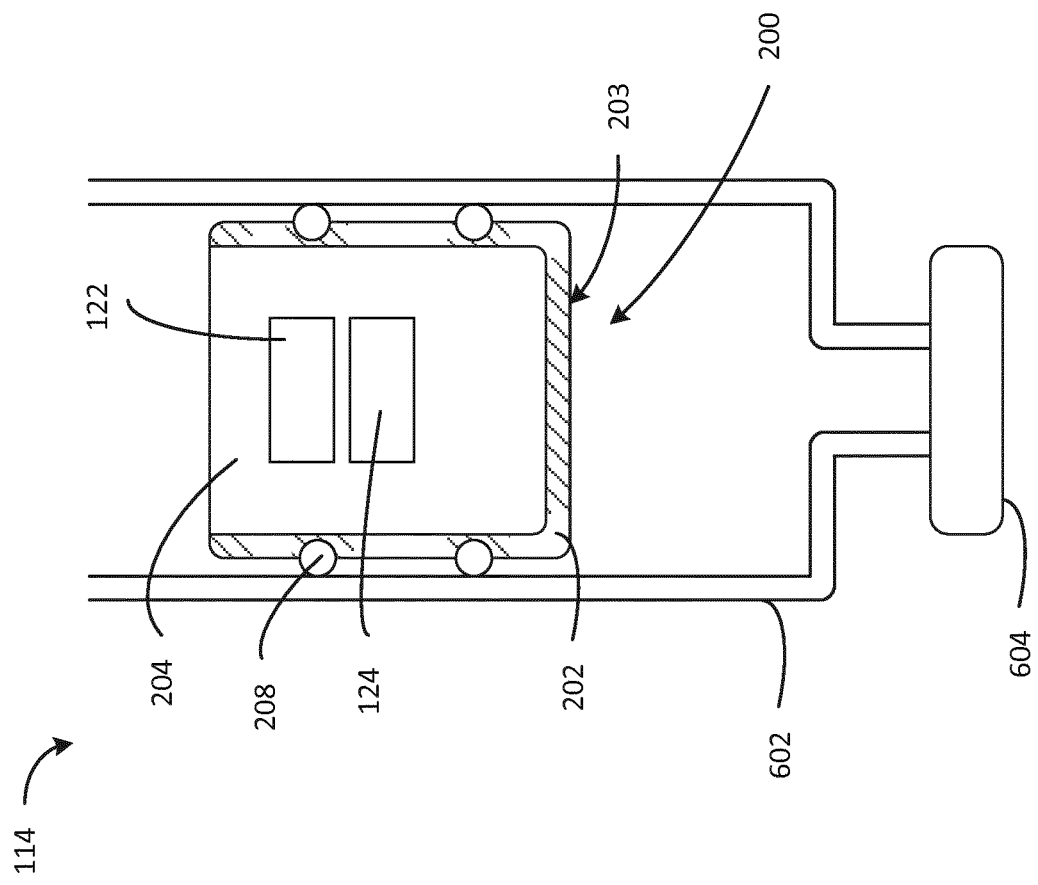
FIG. 2C is a cross sectional view of the stopper of FIG. 2A disposed in the cartridge of the drug delivery device of FIG. 1.

FIG. 2C is a cross-sectional view of the stopper 200 disposed in the cartridge 114. The various features of the stopper 200 shown are described above with respect to FIGS. 2A and 2B. The cartridge 114 includes a housing 602 that interfaces with the sealing element 208 of the stopper 200 to seal an open end of the cartridge 114. In some embodiments, a medicament is disposed in the space between the cap 604 of the cartridge 114 and the shell 202 of the stopper 200.

In some embodiments, different measuring methodologies are used to measure the position of the stopper 200. A certain signal is generated, which changes with the movement of the stopper 200 relative to a fixed position in the system or cartridge 114. This fixed position can be inside of the cartridge 114. In some cases, for example, the fixed position is on the septum area of the cartridge 114 or on another rigid wall of the cartridge 114. Alternatively, an element may be introduced into the cartridge for the purpose of providing a fixed reference. In other embodiments, the fixed reference could be outside of the cartridge outside, such as on the housing of the drug delivery device 100. In some embodiments, a sensor measures the change of a light signal by sending out the light from a light source (e.g., an LED) to the fixed area and receiving the remitted light with a photodetector. The intensity of the remission can be correlated to a distance. Another possibility is to measure the change of time needed for the signal (e.g., an acoustic signal) to travel from a sender to the fixed position back to a receiver positioned close to the sender. In another embodiment, the signal (optical, acoustic, capacitive etc.) can be sent out from a fixed position to a receiver in the moving stopper 200 to measure the change of the signal during stopper travel and correlate it to the stopper position in the cartridge 114.

In an example, a transmitter (e.g., one of the electronics devices 122, 124) transmits an acoustic wave at a first time $t_1$. The first time $t_1$ (e.g., the transmission time of the acoustic wave) may be provided to an external device. The acoustic wave propagates from the transmitter in the stopper 200 toward the distal end of the cartridge 114 (i.e., the end having the cap 604) and is reflected off of (e.g., bounces off of) a surface of the cartridge 114 or a reflector disposed in the distal end of the cartridge 114. A reflection of the acoustic wave (e.g., a reflected wave) propagates from the distal end of the cartridge 114 toward a sensor in the stopper 200. The reflected wave is received at a second time $t_2$. The speed of the acoustic wave is a known speed of sound S in the medicament in the cartridge 114. The elapsed time between transmission and receiving of the acoustic wave is $t_2-t_1$. The elapsed time is multiplied by the speed of sound to determine the distance traveled by the wave from the transmitter, to the distal end of the cartridge 114, back to the sensor. The distance traveled is divided by two to determine the distance between the stopper 200 and the distal end of the cartridge 114, D. The volume V of medicament in the cartridge 114 (e.g., the volume of medicament enclosed in the cartridge 114 between the stopper 200 and the distal end) is determined by multiplying the determined distance by the cross-sectional area A of the cartridge 114 A. Thus, V=A*(t2-t1)*S/2. A detected difference in the determined volume of medicament in the cartridge 114 before and after a drug delivery operation corresponds to the dose administered to the patient.

Figure 3:
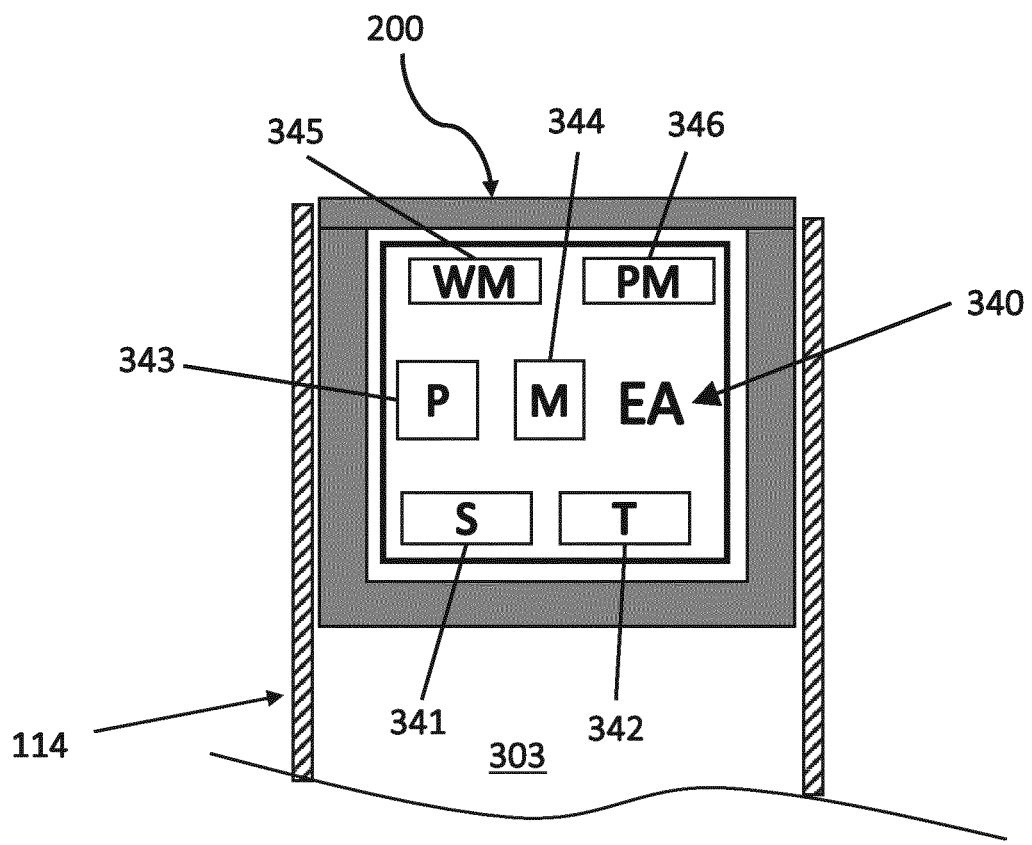
FIG. 3 is a cross-sectional schematic of the internal components of an electronics assembly within the stopper of FIGS. 2A-2C.

FIG. 3 is a cross-sectional schematic of the internal components of an electronics assembly 340, which may be, for example, the electronic components 122, 124 shown in FIG. 1. The electronics assembly 340 is shown disposed in the stopper 200, which is itself installed in the open end of the cartridge 114. The electronics assembly 340 includes a sensor 341, a transmitter 342, a processor 343, a memory 344, a wireless module 345, and power module 346. The sensor 341 and transmitter 342 are arranged in the electronics assembly such that, when the electronics assembly 340 is disposed in the stopper 200, the transmitter 343 is able to emit a sensing signal into the inner volume 303 of the cartridge 114 and the sensor 341 is able to detect a return or reflected signal from the inner volume 303. The processor 343 is operably coupled to all of the elements of the electronics assembly 340 and controls activation of the sensor 341, the transmitter 342, and the wireless module 345. The memory 344 stores instructions for use by the processor 343 in operating the components of the electronics assembly 340, as described above, and discussed in more detail with respect to the following figures.

In operation, the wireless module 346 is configured to communicate with an external electronic device in order to communicate information from the electronics assembly 340. The power module 346 is configured to provide electric power to the all of the components of the electronics assembly 340. In some embodiments, the electronics assembly 340 includes a capacitive device with includes capacitive circuitry configured to receive power wirelessly from, for example, a smartphone via a nearfield communication protocol (NFC) signal, or by a typical wireless charging device with other means of inductive loading, in order to provide energy to the module 346.

Figure 4A:
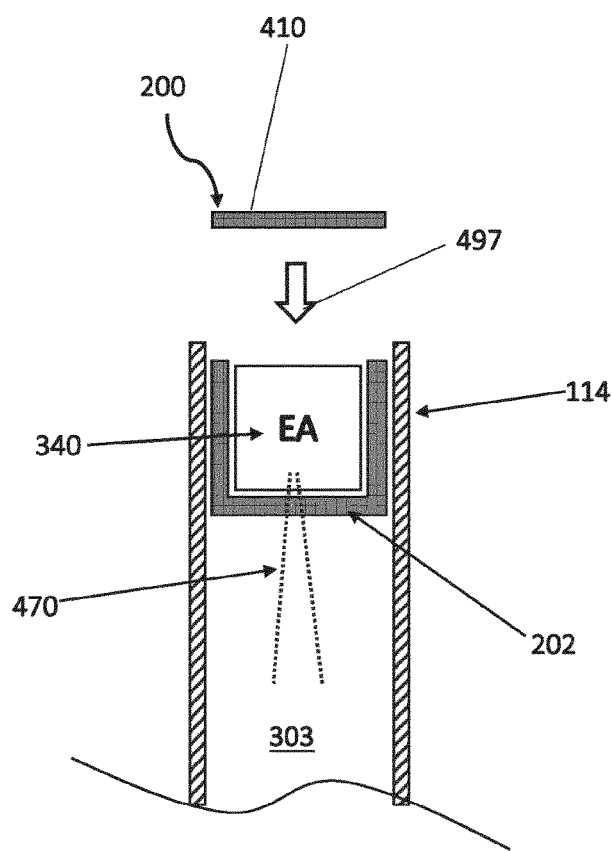
FIG. 4A is a cross-sectional view of the electronics assembly and stopper of FIGS. 2A-2C being disposed in the drug delivery device of FIG. 1.

FIG. 4A is a cross-sectional view of the electronics assembly 340 in the stopper 200, which is configured to be disposed in the drug delivery device 100. The stopper 200 includes the shell 202 holding the electronics assembly 340 and a cap 410 configured to seal the electronics assembly 340 into the stopper 200. FIG. 4A shows the cap 410 being installed 497 during assembly of the cartridge 114, prior to a medicament being filled in the inner volume 303 of the cartridge. In this manner, FIG. 4A represents an assembly step where the electronics assembly 340 is operating in a low-frequency sensing mode to detect, using a sensing signal 470, when the inner volume 303 is filled with the medicament.

In FIG. 4A, the wireless module of the electronics assembly 340 is disabled, and the electronics assembly 340 is in an extremely low power usage state to extend the shelf life of the electronics assembly 340 until the electronics assembly 340 detects that the cartridge 114 is ready for use. In some embodiments, in addition or as an alternative to the low-frequency sensing mode, the electronics assembly 340 includes an activation mechanism configured to trigger the electronics assembly 340 by either being installed in the stopper 200 or in the drug delivery device 100, as shown in FIG. 4B.

Figure 4B:
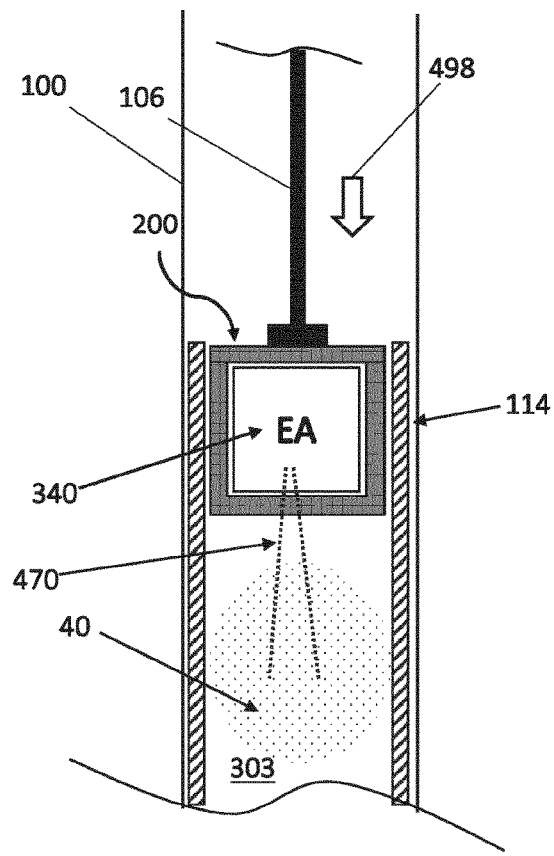
FIG. 4B is a cross-sectional view of the electronics assembly and stopper of FIG. 4A disposed in the drug delivery device of FIG. 1 in a ready-to-use configuration.

FIG. 4B is a cross-sectional view of the electronics assembly 340 and the stopper 200 disposed in the drug delivery device 100 in a ready-to-use configuration. FIG. 4B shows the cartridge 114 and the stopper 200 containing the electronics assembly 340, with the cartridge 114 installed in the drug delivery device 100, with the plunger 106 arranged to drive the stopper 200 and the electronics assembly 340 into the cartridge 114. The cap 410 has sealed the electronics assembly 340 within an interior region of the stopper 200. The inner volume 303 of the cartridge 114 has been filled with a medicament 40, and the electronics assembly 340 is sensing (via sensing signals 470) the presence of the medicament 40 in the inner volume 303. The electronics assembly's detection of the medicament 40 in the cartridge 114 triggers the electronics assembly 340 to change from the low-frequency sensing mode to the high-frequency sensing mode in order to detect a subsequent drug delivery operation in a reasonable time-scale (i.e., so that a user is not waiting too long for activation of the wireless module). In FIG. 4B the plunger 106 is driven by an actuator or drive mechanism of the drug delivery device 100 containing the cartridge 114. In operation, the plunger 106 is driven (as indicated by arrow 498) against the stopper 200 and applies a force to move the stopper 200 into the cartridge 114 in order to drive a portion of the medicament 40 from the cartridge 114.

Figure 4C:
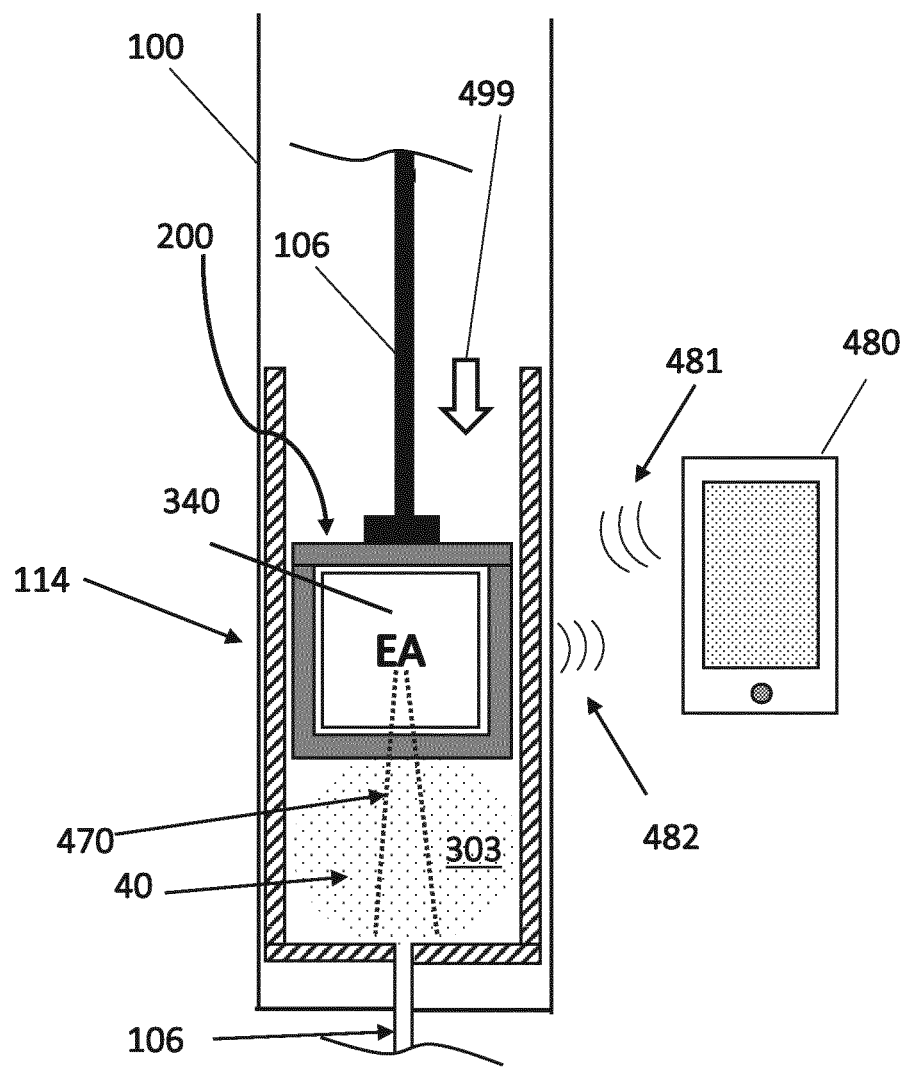
FIG. 4C is a cross-sectional view of the electronics assembly, stopper, and drug delivery device of FIG. 4B after a drug delivery operation.

FIG. 4C is a cross-sectional view of the electronics assembly 340, the stopper 200, and the drug delivery device 100 after a drug delivery operation. FIG. 4C shows the plunger 106 of the drug delivery device 100 contacting the stopper 200 and having driven the stopper 200 into the cartridge 114 (as shown by arrow 499) to conduct a drug delivery operation (e.g., an injection through the needle 109). In operation, the electronics assembly 340 is in a high-frequency mode, after having detected the presence of the medicament 40, and emits a sensing signal 470 that, in some embodiments, is responsive to the position of the stopper 200 in the cartridge 114. The sensing signal 470 is processed by the electronics assembly 340, and the electronics assembly 340 detects the movement of the stopper 200 or the fill level of the cartridge 114 after the illustrated drug delivery operation. In response to the detection of the injection, the wireless module of the electronics assembly 340 is activated for a short duration to enable pairing with an external device 480.

FIG. 4C shows the external device 480 initiating a wireless communication 481 with the electronics assembly 340 and the wireless module of the electronics assembly 340 responding with a return wireless communication 482. In some instances, the return wireless communication 482 to the external device 480 includes the detected change in the fill level of the cartridge 114. In some instances, the return wireless communication 482 includes a history of detected changes in the fill level of the cartridge 114, which enables the external device 480 to receive all or a portion of the prior drug delivery history of the cartridge 114 or the drug delivery device 100. The history of detected changes may include, for example, the previous change, multiple previous changes (e.g., a certain number or over a certain period of time), or a complete history of the detected changes. In some instances, the return wireless communication 482 includes temperature information or a temperature history sensed by the electronics assembly 340. In some instances, the return wireless communication 482 includes batch or expiration information of the medicament, cartridge, or drug delivery device. The return wireless communication 482 can also include any other parameters or changes sensed, detected, or determined by any or all components of the electronics assembly 340. In some embodiments, the return wireless communication 482 includes the state of the electronics assembly or of certain components of the electronics assembly, such as the remaining power. In some instances, the a plunger 106 is a plunger of a syringe where the cartridge 114 is the syringe housing (e.g., a single-use drug delivery device)

Figure 5A:
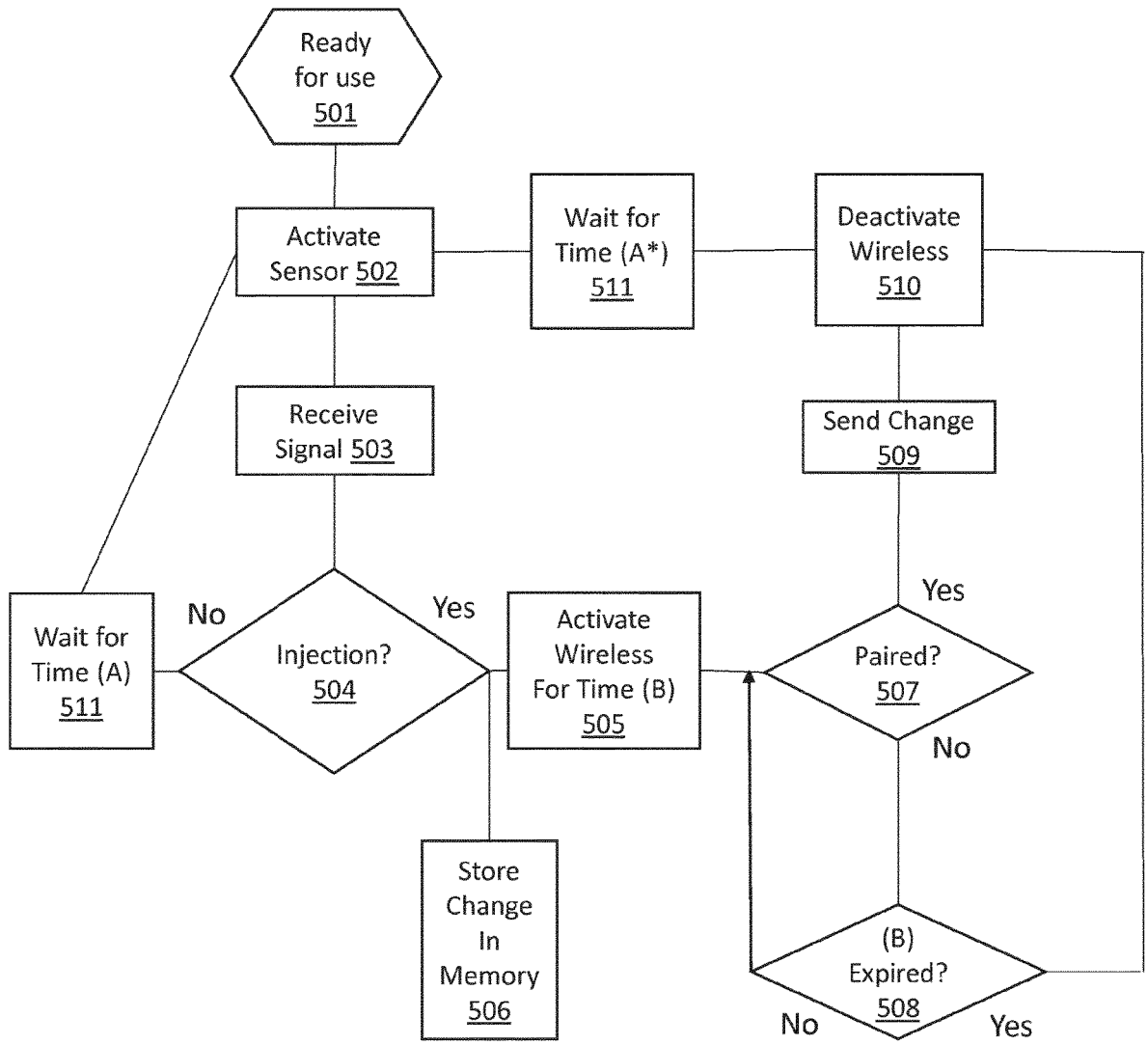
FIG. 5A is a flowchart depicting a method of controlling activation of a wireless module of the electronics assembly.
Figure 5B:
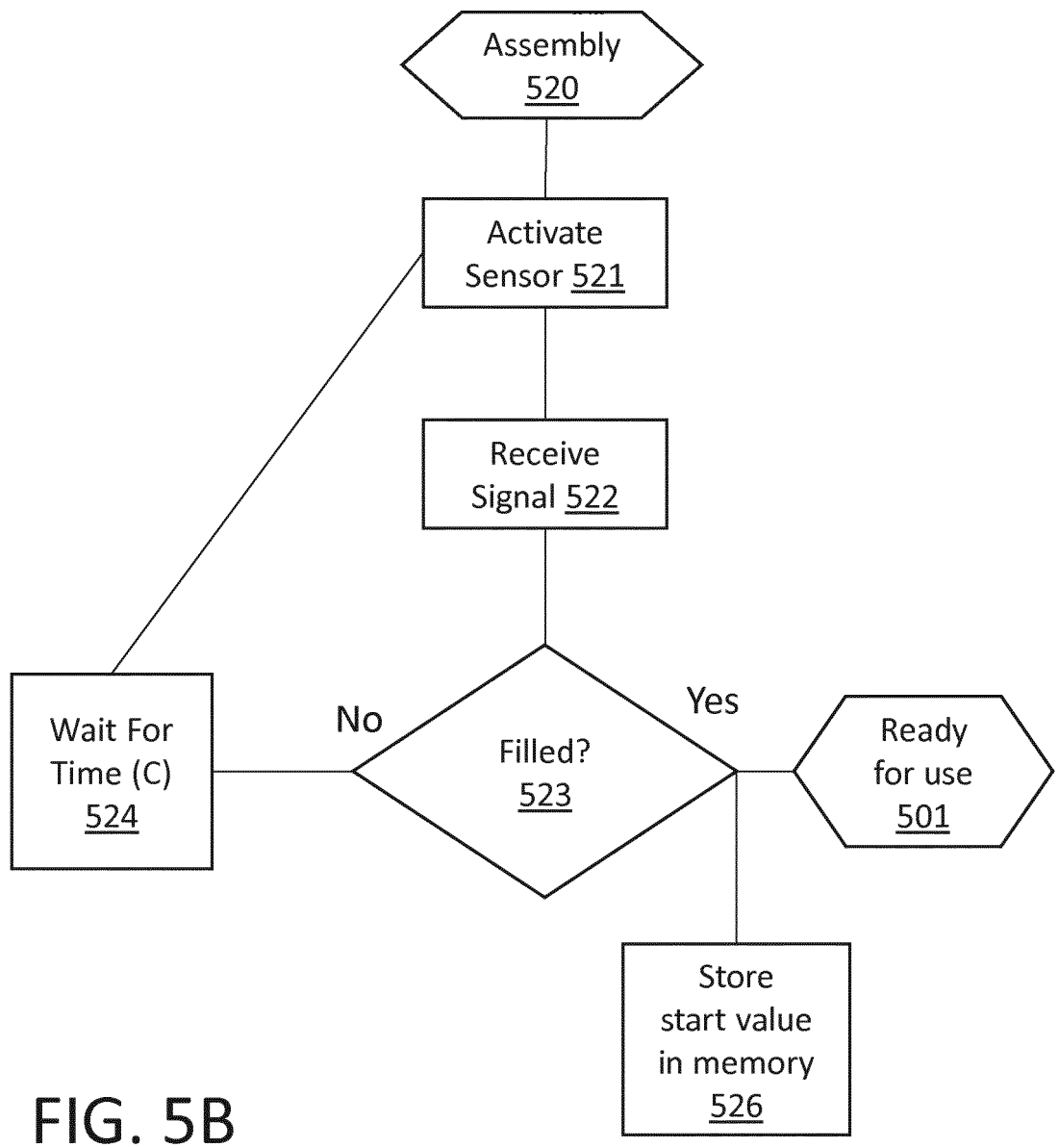
FIG. 5B is a flowchart depicting a method of controlling the sensing duration mode of the electronics assembly.

FIG. 5A is a flowchart depicting a method of controlling activation of the wireless module 345 of the electronics assembly 340. In some examples, the logic of FIGS. 5A and 5B are stored in the memory 344 of the electronics assembly 340 and are executed by the processor 343. With the electronics assembly 340 being in a ready for use state (501), either by a prior detection of the medicament in the cartridge 114 or by triggering of an activation mechanism as described above, the processor 343 activates the sensor (i.e., the sensor 341 and the transmitter 342) (502) to probe the condition of the cartridge 114. The processor receives a signal from the sensor 341 (503) and determines if a change in the fill level of the cartridge 114 is sensed (504). In some instances, the change in the fill level of the cartridge 114 may be sensed as a change in the position of the stopper 200 in the cartridge 114. If no change is determined, the processor 343 waits for a period of time (hereinafter referred to as Time A) (511), which may be, for example 5 minutes, 10 minutes, 15 minutes, or between 1 minute and 1 hour, or some time in between. Generally, Time A is chosen to balance the average detection time and the power usage of the electronics assembly 340. In some instances, the power usage of the sensing operation is extremely small compared to the wireless module 345, and so duration of Time A (the high-frequency mode) may be short enough to allow a user to only wait, at most, a few minutes after an injection for the electronics assembly 340 to be able to pair with the external device 480. In some instances, Time A may be dynamically chosen. For example, if a medicament is administered only once per day, then, after a detected injection, Time A may be set to 12 hours and then reduced to 5 minutes thereafter in order to anticipate the next day's drug delivery operation.

Continuing, if a change in the fill level of the cartridge 114 is determined, then the processor 343 activates the wireless module 345 for a short duration (hereinafter referred to as Time B), which may be, for example 5 minutes, 10 minutes, 15 minutes, or between 1 minute and 1 hour, or some time in between. Generally, Time B is chosen to balance the high power usage of the wireless module 345 with the flexibility in giving the user a larger time window to initiate the pairing of the wireless device. In some embodiments, after a change in the fill level is determined, the processor 343 instructs the further sensing operations to occur rapidly until no further change is detected, in case the initial detection was made during a drug delivery operation and not immediately subsequent to the completion of the operation. In addition, in some embodiments, the processor 343 stores the detected change in the fill level in the memory 344 (506). While the wireless module 345 is activated, the external device 480 is able to pair with the electronics assembly 344. While the wireless module 345 is activated, the processor checks if a pair is detected (507). If no pairing is detected, then the processor checks to see if Time B has expired (508). If no pairing is detected at the end of Time B, then the wireless module 345 is deactivated (510) and the electronics assembly returns to the high-frequency sensing mode (i.e., the ready for use state 501). When a pairing is detected, the wireless module 345 transmits the detected change to the external device 480 (509) and deactivates the wireless module 345 (510). After the deactivation, as described above, the processor 343 may return to the high-frequency mode to detect a subsequent drug delivery operation, or wait the Time A* (which may be the same as Time A, or a different time specifically chosen to occur only after a detected drug delivery operation) (511) before returning to the high-frequency detection mode.

FIG. 5B is a flowchart depicting a method of controlling the sensing duration mode of the electronics assembly 340. As discussed in more detail above, in some instances, the electronics assembly 340 uses an activation mechanism to enter the ready for use state 501 prior to final assembly of the drug delivery device, and, in some instances, the electronics assembly 340 uses a low-frequency sensing mode, as shown in FIG. 5B, to detect the ready for use state 501. In the low-frequency sensing mode, the electronics assembly 340 is in an assembled state, which may include the final assembly of the components of the electronics assembly 340 or an activation step during assembly of the electronics assembly into the cartridge 114 or drug delivery device prior the filling of the cartridge with a medicament (i.e., the final assembly of the drug delivery device to make it ready for use) (520). In this assembled state, the processor 343 343 activates the sensor (i.e., the sensor 341 and the transmitter 342) (521) to probe the condition of the cartridge 114. The processor receives a signal from the sensor 341 (522) and determines if a medicament is detected in the cartridge 114 (523). In some instances, the filling of the medicament in the cartridge 114 may be sensed as a change in the position of the stopper 200 in the cartridge 114. If no filling is determined 523, the processor 343 waits 524 for a period of time (hereinafter referred to as Time C), which may be, for example 12 hours, 24 hours, 48 hours, between 1 hour and 1 day, or some time in between. In some instances, Time C is chosen to balance the power usage of the electronics assembly 340 to enable a long shelf life of the electronics assembly after construction with the expected time between the drug delivery device being filled with a medicament and an expected use by a patient. Time C can be chosen to ensure that the electronics assembly is in the ready for use state 501 before the drug delivery device has been delivered to a patient for use. When the medicament is detected in the cartridge 114, the processor stores the initial sensed valve in memory 344 (526) for use in later determining when the fill level has changed to indicate a drug delivery operation has occurred.

Described above are devices are methods for providing energy to electronic circuitry in cartridge systems (for example, those disclosed herein) using a power module (PM), which may include, for example, batteries or other power storage devices, using such technologies as lithium ion, nickel-metal hydride, nickel-cadmium, zinc-air, or the like.

Aspects of the systems disclose above enable medical injectors to employ 'smart' technologies by way of an attached of the included electronic components (e.g. RFID, sensor) to give a certain features to a cartridge of a drug delivery device (e.g. of a pen-type injector). When integrating electronics into the stopper of a cartridge, a one or more components may be active (e.g., a sensor to measure certain properties of the injector or cartridge) and require an energy source, which typically could be a battery. One alternative is to use a means of energy harvesting as a power source replacement for a battery. In some instances, a light source, such an LED or laser light source, is included in the drug delivery device and the electronics assembly includes a receptacle (e.g., a photovoltaic unit or a light sensor) that is configured to receive light from the light source. In some instances, the receptacle is configured to switch the electronics assembly on or off upon receipt or termination of the light incident on the receptacle, or, in some instances, the receptacle provides power to the electronics assembly by converting the received light into electric energy.

Embodiments of the present disclosure can also apply to prefilled single and double chamber syringes that may not use a cartridge. The examples described above for electronics assemblies in the stopper of a cartridge can also be used with other drug containers, such as disposable prefilled syringes or reusable/refillable cartridges. In some instances, the electronics assembly is contained in the cartridge or in the drug delivery device in a manner enabling the electronics assembly to sense a change in the fill level of the cartridge or syringe after an injection. In some instances, components of the electronics assembly are located outside of the stopper or in different parts of the cartridge or drug delivery device.

Some of the features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described embodiments by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

A number of embodiments of the present disclosure have been described. Nevertheless, it will be understood that various modifications may be made without departing from the spirit and scope of the present disclosure. Accordingly, other embodiments are within the scope of the following claims.

A number of embodiments of the present disclosure have been described. Nevertheless, it will be understood that various modifications may be made without departing from the spirit and scope of the present disclosure. Accordingly, other embodiments are within the scope of the following claims.

The invention claimed is:

1. An electronics assembly for use in a drug delivery device, comprising:
a processor;
a sensor arranged to measure a fill level of a drug container of the drug delivery device and transmit a measurement signal to the processor that indicates the measured fill level;
a wireless module for communicating with an external device;
a power module arranged to supply power to the sensor, the processor, and the wireless module; and
at least one non-transitory computer readable medium storing instructions operable to cause the processor to perform operations comprising:
activating the sensor at a first time interval to receive the measurement signal;
determining, based on the received measurement signal, if the drug container contains medicament;
stopping, when the drug container is determined to contain medicament, the activating of the sensor at the first time interval;
activating, after stopping the activating of the sensor at the first time interval, the sensor at a second time interval to receive the measurement signal, the second time interval being shorter than the first time interval;
determining, for each activating of the sensor at the second time interval and based on the received measurement signal, a change in the fill level of the drug container; and
activating, when the change in the fill level is detected, the wireless module for a first duration to enable the wireless module to pair with the external device.

2. The electronics assembly of claim 1, wherein the operations further comprise:
transmitting, when the wireless module is paired with the external device, data representing the change in the fill level of the drug container to the external device; and
deactivating the wireless module.

3. The electronics assembly of claim 1, further comprising a switch arranged to be activated by assembly of the electronics assembly into the drug delivery device such that the switch activates the electronics assembly.

4. The electronics assembly of claim 1, wherein the second time interval is less than one hour.

5. The electronics assembly of claim 4, wherein the first time interval is more than 12 hours and the first duration is less than 30 minutes.

6. The electronics assembly of claim 1, wherein the operations further comprise:
determining a remaining power level of the power module; and
adjusting the first duration based on the remaining power level.

7. The electronics assembly of claim 1, wherein the operations further comprise: storing each change in the fill level of the drug container in memory;
transmitting, when the wireless module is paired with the external device, data representing each of the stored changes in the fill level of the drug container to the external device; and
deactivating the wireless module.

8. The electronics assembly of claim 1, wherein:
the sensor is arranged inside of a bung; and
the bung is configured to be inserted into the drug container.

9. The electronics assembly of claim 1, wherein the electronics assembly is configured to be inserted into a bung.

10. The electronics assembly of claim 1, wherein one or more of the electronics assembly or the sensor is integrally formed with a bung.

11. The electronics assembly of claim 8, wherein:
the sensor is configured to measure the fill level of the drug container by measuring a position of the bung in the drug container; and
the operations comprise determining the fill level of the drug container based on the measured position of the bung.

12. The electronics assembly of claim 1, wherein:
the sensor comprises an ultrasonic transmitter and a corresponding detector;
the ultrasonic transmitter is configured to emit an ultrasonic signal into the drug container; and
the corresponding detector is configured to receive a reflection of the ultrasonic signal from the drug container and transmit the measurement signal to the processor.

13. The electronics assembly of claim 1, wherein the external device comprises one of: a smart phone, a smart watch, a tablet, or a personal computer.

14. The electronics assembly of claim 1, wherein:
the drug delivery device or the drug container comprises printed identification information or expiration information; and
the operations further comprise: transmitting, when the wireless module is paired with the external device, the printed identification information or expiration information.

15. A system comprising:
a drug delivery device comprising a housing;
a drug container configured to be contained in the housing of the drug delivery device; and
a bung disposed in a cavity of the drug container and configured to be driven into the drug container by a drive mechanism of the drug delivery device, the bung comprising an electronics assembly comprising:
a processor;
a sensor arranged to measure a fill level of the drug container and transmit a measurement signal to the processor that indicates the measured fill level;
a wireless module for communicating with an external device;
a power module arranged to supply power to the sensor, the processor, and the wireless module; and
at least one non-transitory computer readable medium storing instructions operable to cause the processor to perform operations comprising:
activating the sensor at a first time interval to receive the measurement signal;
determining, based on the received measurement signal, if the drug container contains medicament;
stopping, when the drug container is determined to contain medicament, the activating of the sensor at the first time interval;
activating, after stopping the activating of the sensor at the first time interval, the sensor at a second time interval to receive the measurement signal, the second time interval being shorter than the first time interval;
determining, for each activating of the sensor at the second time interval and based on the received measurement signal, a change in the fill level of the drug container; and
activating, when the change in the fill level is detected, the wireless module for a first duration to enable the wireless module to pair with the external device.

16. The system of claim 15, wherein:
the sensor is configured to measure the fill level of the drug container by measuring a position of the bung in the drug container; and
the operations comprise determining the fill level of the drug container based on the measured position of the bung.

17. The system of claim 15, wherein the operations further comprise:
transmitting, when the wireless module is paired with the external device, data representing the change in the fill level of the drug container to the external device; and
deactivating the wireless module.

18. The system of claim 15, wherein:
the second time interval is less than one hour;
the first time interval is more than 12 hours; and
the first duration is less than 30 minutes.

19. A system comprising:
a drug delivery device comprising a housing;
a drug container configured to be contained in the housing of the drug delivery device, the drug container comprising:
a bung disposed in a cavity of the drug container and configured to be driven into the drug container by a drive mechanism of the drug delivery device; and
an electronics assembly comprising:
a processor;
a sensor arranged to measure a fill level of the drug container and transmit a measurement signal to the processor that indicates the measured fill level;
a wireless module for communicating with an external device;
a power module arranged to supply power to the sensor, the processor, and the wireless module; and
at least one non-transitory computer readable medium storing instructions operable to cause the processor to perform operations comprising:
activating the sensor at a first time interval to receive the measurement signal;
determining, based on the received measurement signal, if the drug container contains medicament;
stopping, when the drug container is determined to contain medicament, the activating of the sensor at the first time interval;
activating, after stopping the activating of the sensor at the first time interval, the sensor at a second time interval to receive the measurement signal, the second time interval being shorter than the first time interval;
determining, for each activating of the sensor at the second time interval and based on the received measurement signal, a change in the fill level of the drug container; and
activating, when the change in the fill level is detected, the wireless module for a first duration to enable the wireless module to pair with the external device.

20. The system of claim 19, wherein the operations further comprise:
    transmitting, when the wireless module is paired with the external device, data representing the change in the fill level of the drug container to the external device; and
    deactivating the wireless module.

\* \* \* \* \*